(12) United States Patent
Heck

(10) Patent No.: US 7,036,514 B2
(45) Date of Patent: May 2, 2006

(54) INTRA-ORAL CAVITY SURGICAL DEVICE

(75) Inventor: Janise E. Heck, 876 Oakmoor Dr., Fenton, MO (US) 63026

(73) Assignees: Janise E. Heck, Fenton, MO (US); George R. Schoedinger, III, St. Louis, MO (US); John B. Weltmer, St. Louis, MO (US)

( * ) Notice: Subject to any disclaimer, the term of this patent is extended or adjusted under 35 U.S.C. 154(b) by 496 days.

(21) Appl. No.: 09/683,940

(22) Filed: Mar. 5, 2002

(65) Prior Publication Data

US 2003/0170590 A1    Sep. 11, 2003

(51) Int. Cl.
*A61C 5/14* (2006.01)
(52) U.S. Cl. ........................ 128/859; 128/861
(58) Field of Classification Search ............ 128/848, 128/859–862; 602/41–45
See application file for complete search history.

(56) References Cited

U.S. PATENT DOCUMENTS

| | | | | |
|---|---|---|---|---|
| 3,705,585 A | * | 12/1972 | Saffro | 604/385.01 |
| 3,885,508 A | * | 5/1975 | Hofmann et al. | 112/475.08 |
| 3,916,879 A | * | 11/1975 | Cotten | 600/242 |
| 4,430,013 A | * | 2/1984 | Kaufman | 401/132 |
| 4,665,901 A | * | 5/1987 | Spector | 601/139 |
| 6,042,575 A | * | 3/2000 | Osborn et al. | 604/387 |
| 6,436,384 B1 | * | 8/2002 | Santoiemmo | 424/76.6 |
| 6,727,445 B1 | * | 4/2004 | Cullinan et al. | 200/85 R |

* cited by examiner

*Primary Examiner*—Michael A. Brown
(74) *Attorney, Agent, or Firm*—Blackwell Sanders Peper Martin LLP

(57) ABSTRACT

An intra-oral cavity device for preventing contact between upper and lower teeth of an anesthetized patient. The device includes an elongate pillow that when gripped between the teeth of a patient, prevents contact between the teeth and/or gums and thereby prevents damage to the teeth and/or gums. The pillow may be made of a fibrous, porous and/or absorbent material. The device is adapted for single use and thus disposal after use by a patient. A method of the use of performing surgery using such a device is also provided.

18 Claims, 2 Drawing Sheets

INTRA-ORAL CAVITY SURGICAL DEVICE

BACKGROUND OF INVENTION

Many surgical procedures are performed while the patient is anesthetized. While under the influence of the anesthesia, the surgical patient oftentimes will incur damage to their teeth. Typically, the damage is done while the patient is going under or waking up. During surgery, the patient is oftentimes given muscle relaxers which reduces hard biting and grinding reducing the risk of tooth damage during this portion of the surgical procedure. Teeth can break from hard biting or damage can be due to grinding of the teeth which can produce chipped teeth and even broken teeth. Additionally, during some surgical procedures, the anesthetized patient will have an endotracheal tube or an LMA (laryngeal mask airway) inserted between the teeth and partially down the throat for providing air and/or other gases to the lungs. This tube can exacerbate surgical problems of the surgical patient by the patient biting down which can crimp the hose thereby limiting or preventing flow of gas therethrough possibly causing pulmonary edema, hypoxia, hypercabia or perhaps cause damage to the front teeth. As few as two missed breaths can injure the patient, including causing pulmonary edema. If teeth are damaged they need to be repaired which adds to the expense of the surgical procedure. It is not uncommon for the surgeon to pay for dental work rather than turn a claim over to their insurance carrier because of the potential increase in insurance premiums.

While devices are known for placing between a patient's teeth to prevent tooth damage, they have drawbacks. For example, mouth guards such as those worn by athletes need to be formed to shape prior to use. They are also placed between all of the teeth preventing access for a gas tube as is sometimes required for surgery. Further, such guards tend to be expensive and require effort by the hospital staff and patient to make ready to use. Other tooth guards are known and are made out of either plastic or other elastomeric material, therefore, for all practical purposes are non-porous and are also relatively thin in the area between the teeth. Because they are thin, the teeth are not spaced far enough apart to provide access for the gas tube. If such polymeric or plastic guards are made thicker, then the weight and expense likewise increase and are non porous or absorbent. Further, plastic or elastomeric guards, even though resilient, have little deformation under load and if the teeth are opened slightly, then there is no more tooth force on the guard to retain it in place between the teeth. Elastic and polymeric materials can, when deformed in one direction, apply relatively high resulting forces in other than the direction of compressive biting force which could cause unwanted lateral forces on the teeth. Elastomeric and polymeric protectors may also be cut by some teeth in use risking severing a portion that could injure the patient.

It is also recommended to monitor certain physiological aspects of a patient during surgery, e.g., the patient's temperature. Also, some patients will expectorate fluids, such as bile or stomach contents into the oral cavity potentially causing problems. Temperature sensors such as those carried by esophageal stethoscopes are used to monitor a patient's temperature by contacting the soft tissue in the oral cavity with the sensor which is connected to a monitor showing and/or recording the sensed temperature. Temperature monitoring is important to keep the patient from getting too cold or too hot.

There is thus a need for an improved surgical device to protect teeth and/or gums from damage during the surgical procedure.

SUMMARY OF INVENTION

The present invention involves the provision of a surgical device for use intra-orally to guard teeth and/or gums from damage when the surgical patient is anesthetized. The device includes a pillow comprising a porous, absorbent and/or fibrous material having one transverse dimension adequate to hold the teeth spaced apart sufficient under biting load to allow the use of a gas tube inserted between the front teeth. The length of the pillow can be such as to allow a portion to be placed between the teeth from the rear of the teeth toward the front of the teeth having sufficient length left over to be extra-oral to provide for grasping for insertion and removal and to allow a member of the surgical team to monitor the location of the pillow during surgery. Means is provided to maintain the pillow as a monolithic structure preventing portions of the pillow from separating during the surgical procedure. A tab may be provided for positioning extra-orally to assist in removal and may be secured as by taping to the patient to help secure the pillow in place.

The present invention also allows for the provision of, in a surgical patient, a pillow positioned in an oral cavity. A portion of the pillow is positioned between teeth in the oral cavity while being adapted to also have an extra-oral portion projecting from the oral cavity. The portion between the teeth and/or gums holds the teeth and/or gums spaced apart. The pillow is elongate and comprises absorbent, fibrous and/or porous material and has a relaxed transverse dimension adequate to allow for it to be retained in place during movement of the teeth and/or gums during the surgical procedure and to keep the teeth and/or gums separate when biting force is applied thereto. Means is associated with the pillow and maintains the pillow as a monolithic structure both inside and outside of the oral cavity.

The invention is also directed to the provision of a method of treating a surgical patient by preparing a patient for surgery with the patient having an oral cavity. At least one pillow is placed in the oral cavity whereby a portion of the pillow may be extra-oral and at least a portion of the pillow is intra-oral. The pillow is elongate and comprises absorbent, fibrous and/or porous material. A portion of the intra-oral portion of the pillow is positioned between molars and/or molar gum area to maintain the teeth and/or gums in the oral cavity spaced apart during at least a portion of the surgery. Surgery is performed on the patient with the pillow being retained between the teeth and/or gums of the patient by the patient. After surgery, the pillow is removed from the oral cavity and disposed of.

BRIEF DESCRIPTION OF DRAWINGS

Like numbers throughout the various figures designate like or similar parts.

DETAILED DESCRIPTION

Figure 1:
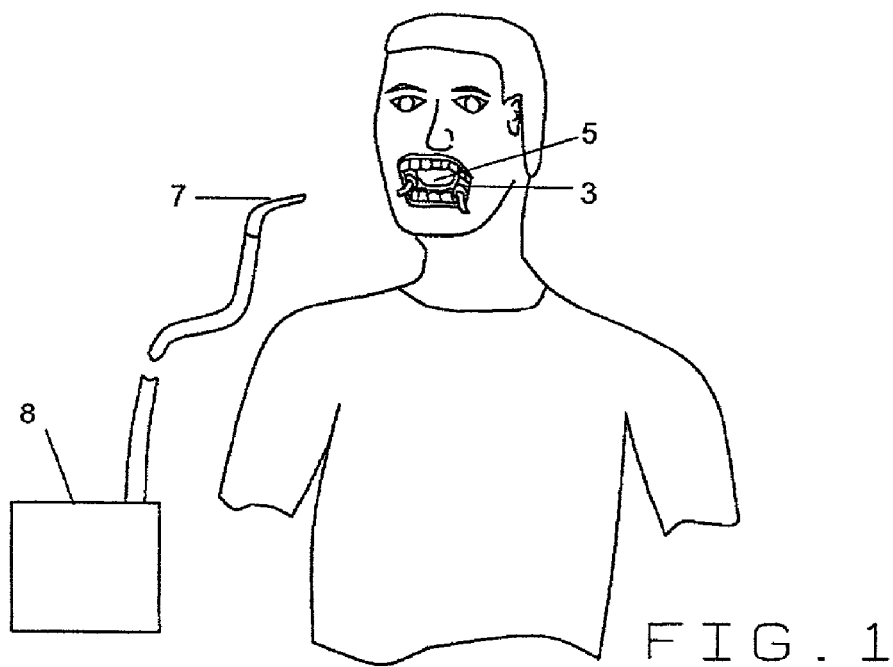
FIG. 1 is a perspective view of an intra-oral cavity surgical device shown in place in a surgical patient with the patient being shown.
Figure 2:
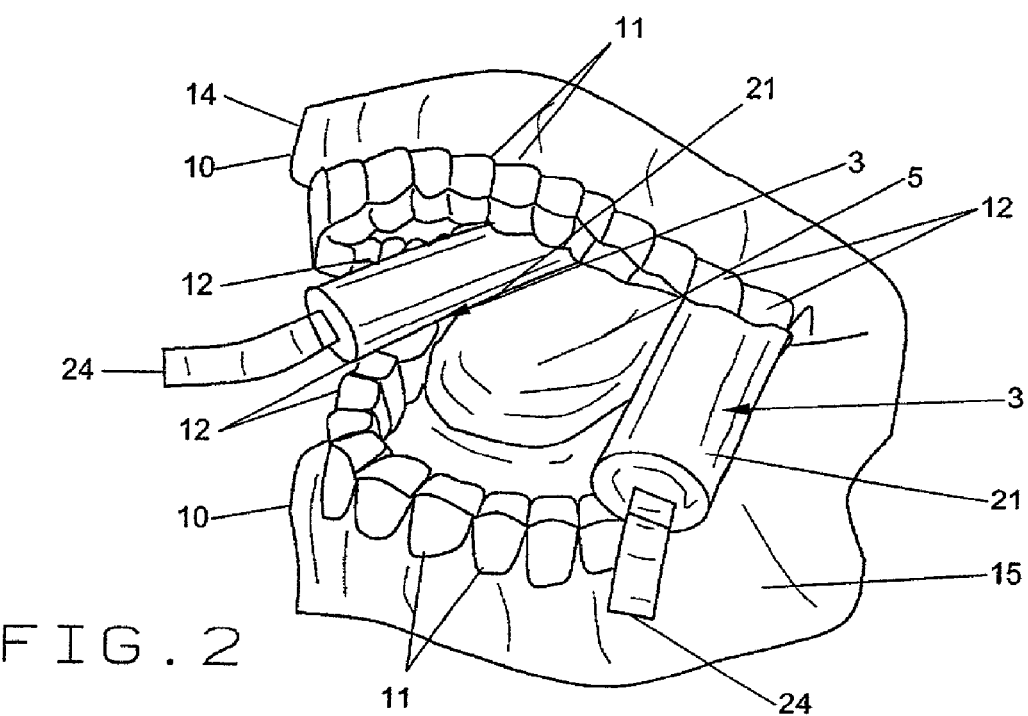
FIG. 2 is an enlarged perspective view of an oral cavity with a pair of the surgical devices in place.

As illustrated in FIGS. 1 and 2, a surgical patient, such as a human, has an oral cavity 5 in which is placed one or more cushion devices. During surgical procedures, a tube 7, e.g., an endotracheal tube or LMA, may be inserted into the oral cavity to provide gas for the surgical patient or for other purposes. Gas is supplied from a source 8 of gas such as a pressurized tank or a pump. The oral cavity 5 includes teeth projecting from gums 10 with the teeth including front teeth designated generally 11 and molars designated generally 12. The teeth 11 and 12 are in both the upper (maxilla) and lower (mandible) jaws 14 and 15 respectively. It is to be noted that some patients may not have teeth or only a few teeth or false teeth and therefore, as used herein and in the claims, between the gums means between the upper and lower teeth, where and if present, and/or gums unless otherwise indicated. Even though a portion of the device 3 may be between teeth, it is also between the gums. False teeth are usually removed from a patient prior to being anesthetized.

Figure 3:
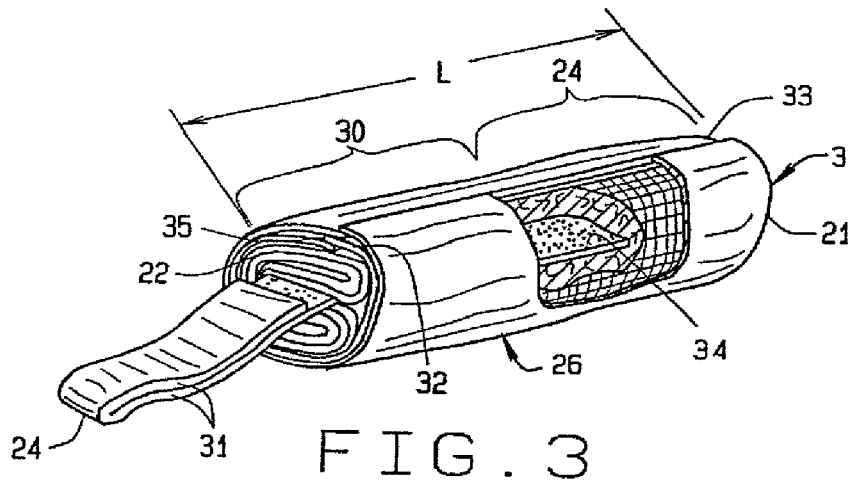
FIG. 3 is a perspective view of the intra-oral surgical device with portions broken away to show internal details.

As best seen in FIGS. 1 and 2, an intra-oral device 3 that includes a pillow 21 that is shown in detail in FIG. 3, is positioned between the upper and lower-jaws 14 and 15 on at least one side of the mouth or one on each side of the mouth, to be retained between the upper and lower gums along the side gums and if the patient has teeth, between the upper and lower rear teeth 12.

As seen in FIG. 3, an intra-oral cavity cushion device 3 is provided. The device 3 includes a pillow 21, a finger tab 24 and means designated generally 26 for maintaining the pillow as a monolithic structure during storage, use and removal. In the form of the invention shown in FIG. 3, the pillow 21 is comprised of a fibrous and/or porous (formed by interstitial spaces between the fibers and threads) material such as absorbent cotton. The fibrous material may be woven, knit or felt which is absorbent and porous and may be of natural fiber or synthetic fiber or a combination thereof. In a preferred embodiment, the material can be a cotton gauze 22 (a woven material) rolled into an elongate roll. The tightness of the roll will determine the firmness and compressibility of the pillow 21. It is preferred that under the anticipated force of biting by the patient, that when compressed, the pillow have a transverse dimension of at least about ¼ inch and preferably between the gums in the range of between about ¼ inch and about ½ inch to provide adequate space between the front teeth and/or gums 11 for the tube 7 to prevent its being occluded. Preferably, the gauze is a woven gauze as is well known in the art and can be clean and/or sterile as delivered to the surgeon for use. It has been found that a pillow 21 having a transverse dimension, which for example, in a round cross section execution is the diameter of the pillow 21 with a diameter being at least about ⅜ inch and preferably in the range of between about ⅜ inch and about 1 inch (in a relaxed or unloaded condition) to provide sufficient support to hold the teeth spaced adequately for positioning the tube 7 between the front teeth. The pillow 21 has two portions which will vary in length depending on the patient's teeth and/or gum size. An intra-oral portion is designated by the bracket 29 and an extra-oral portion is designated by the bracket 30. In a preferred embodiment, the length of the pillow 21 designated L in FIG. 3 is in the range of between about 1½ inches and about 3½ inches. Typically, the intra-oral portion 29 has a length in the range of between about 1½ inches and 2½ inches with the remainder, if any, of the length of the pillow 21 being the extra-oral portion, i.e., that portion that may project from the patient's mouth during use. The size of the oral cavity, gums and/or teeth of the patient and/or how far in the pillow needs to be inserted will determine how much of the pillow is intra-oral and how much is extra-oral. In some cases, the entire length of the pillow may be intra-oral.

In the form of invention shown in FIG. 3, the pillow 21 comprises a fibrous woven gauze. The pillow can be advantageously produced by forming the gauze 22 into a roll. This can be accomplished by rolling five three by three inch squares of gauze, each having four layers of material. The exterior layer can be an unfolded layer of gauze 32 having two layers wrapped tightly around the inner layers of gauze. Such an execution is particularly advantageous when making the pillow 21 by hand. In mass production, other forms and arrangements of fibrous material may be used. For example, the inner layers of material may be random fibers or random pieces of woven, knit or felt like material wrapped inside an outer layer which forms a continuous sheet of material enclosing the inner material.

A finger tab 24 is provided to assist in handling of the pillow 21 by the surgeon or other personnel working in the operating room, for example, the anesthesiologist. The finger tab 24 is preferably flexible to help prevent injury to the patient and to provide a means of securing the intra-oral device to the patient. A preferred finger tab 24 is an elongate ribbon of adhesive backed fabric having one end projecting from an end of the pillow 21 and a portion of the length thereof positioned between contacting surfaces of the material forming the pillow 21. The tab 24, for example, can be a synthetic or natural fiber material, can have a width in the range of between about ¼ inch and about ½ inch, and is clean and/or sterile when used by medical personnel. The tab may also be polymeric. The tab 24 in a preferred embodiment has the exposed end thereof folded over where two adhesive backed face portions 31 engage one another such that the tab is substantially free of adhesive on at least two exterior surfaces, i.e., the adhesive is not generally exposed. The other end 34 has exposed adhesive that adheres the tab 24 to the pillow 21, for example, by adhesively being secured to a layer of a sheet of the fabric comprising the pillow 21, either one of the interior sheets or the exterior sheet.

Means 26 is provided to retain the pillow 21 as a monolithic structure with a sheet exterior. In the case of the structure illustrated in FIG. 3, the means 26 includes a retainer 33 that prevents the exterior sheet and interior material from unrolling or separating. The retainer 33 includes an adhesive tape such as Tegaderm which can encircle the pillow 21 around a substantial part thereof and is secured to the exterior fabric sheet or encircle the entirety of the pillow's outer periphery and be secured to itself and the exterior fabric sheet. It also may extend along substantially the entire length of the pillow. The retainer 33 preferably bridges the exposed end 35 of the exterior fabric sheet of the pillow 21 and is adhesively secured to the pillow material on both sides of the end 35 to prevent unrolling. The tape comprising the illustrated retainer preferably has an adhesive coating that is water resistant to prevent the adhesive from becoming unattached from the pillow 21 or itself when moisture from the oral cavity is exposed thereto or from the pillow if wetted prior to use. The tape should be flexible and be cut and tear resistant and may be polymeric. Adhesive tape is particularly advantageous because it will not cause any physical damage to the patient and is readily flexible to conform to the shape of the pillow when it is either stored or deformed during use. A shrinkable polymeric tube or elastic band can be used as an alternate to or in combination with an adhesive tape retainer 33.

Figure 4:
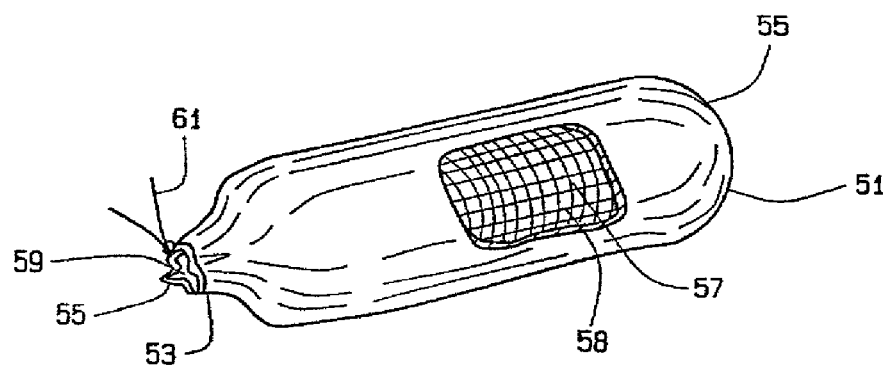
FIG. 4 is a fragmentary perspective view of an alternate embodiment of the present invention.

FIG. 4 shows a first alternative embodiment of the present invention and comprises a pillow designated generally 51. In this alternate form of invention, the pillow 51 is comprised of a tubular covering or sock 53 which can be made of a sheet of woven, knit or felt fabric made of fibrous material such as natural, synthetic or a combination of fibers like cotton, polyester or the like. The cover 53 may be formed with a seam or seamless in its elongate or longitudinal dimension and has normally closed ends 55, only one being shown in FIG. 5. The cover 53 has an interior 57 that can be filled with fibrous, porous and/or absorbent material 58 such as natural or synthetic fibers like cotton or polyester, a sponge-like material such as cellulosic or elastomeric sponge. The fibrous material may be random fibers compressed in the covering 53 or rolled sheet material. As shown, one end 55 has a selectively sealable opening 59 that can be expanded or contracted by use of a drawstring 61. The material 58 may be inserted through the opening 59 and then by pulling of the drawstring 61, the opening 59 can be closed to prevent loss of the material 58. The drawstring 61 can also serve as a finger tab like the tab 24. The dimensions and compressibility of the device 51 can be the same as the dimensions and compressibility of the device 21. Further, the drawstring 61 serves the same function as the tape 33 providing means for preventing the material 58 from separating from the pillow and retaining the pillow as a monolithic structure.

Figure 5:
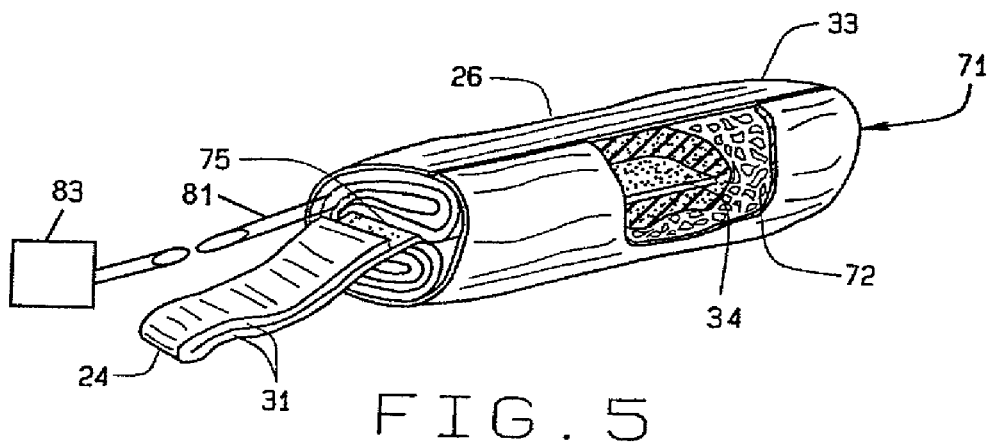
FIG. 5 is a fragmentary perspective view of a second alternate embodiment of the present invention.

FIG. 5 shows a second alternative embodiment of the present invention. In this embodiment, the pillow designated generally 71 is made of a foam or sponge-like material either cellulosic or elastomeric with interstitial voids. The pillow 71 has the same dimensions and characteristics as those described for the pillows 21 and 51. The pillow 71 may include a tube such as the tube 53 shown in FIG. 4 or may have the exterior of the foam material exposed for contact with the patient. The pillow 71 may be made by rolling the foam or sponge material 72 in a spiral or other suitable pattern like the pillow 21. Also, the pillow 71 is a monolithic structure and may be made by forming the pillow such as by cutting or molding, not requiring any additional rolling or the like. A tab 24 may be provided by adhesively securing it to the pillow 71. Alternatively, a slot or opening 75 may be cut or otherwise formed in the pillow 71 with the tab 24 having a portion thereof inserted into the slot 75 and being adhesively secured to the pillow 71. If the pillow 71 is made by rolling foam or sponge material in a spiral pattern or other pattern (as shown), then the tab 24 may extend through the opening 75 and be secured between surfaces of the foam comprising the pillow 71 as the tab 24 is secured in the pillow 21. In the event the pillow is made by rolling foam material, means 26 such as that used for the pillow 21 may be utilized to retain the pillow 71 as a monolithic structure during storage and use.

In use, any of the three disclosed embodiments or other embodiments of the present invention are used during a surgical procedure where the patient is anesthetized by having a sheet of fabric such that the exterior and interior material will remain as part of the intra-oral device and the device will remain as an integral structure. Further, the use of a retainer as described also helps prevent the dislodging of fibers from either the interior or exterior of the device as well as reducing the shearing of any material from the device if it is of a foam or sponge-like structure. Prior to being anesthetized, the size of the oral cavity will be estimated to determine the appropriate size of device and pillow. Prior to inserting the device into the oral cavity and between the gums, the pillow may be wetted with water, but is preferred that the pillow be able to absorb water in an amount of at least about ¼ of its relaxed volume. The mouth of the patient is opened and the device is installed. Only one may be used or alternatively, one between each side of the mouth leaving, if desired, an extra-oral portion and the tab positioned extra-orally. By wetting the device, the device can be conformed to a shape with the wetness helping the device retain that shape to facilitate insertion of the device in the appropriate location in the mouth. Further, wetting can help reduce mouth dryness during the surgical procedure. If desired, the finger tab 24 may be secured to the patient, for example, by taping it to the cheek which will help prevent dislodgment of a pillow 21 from the mouth and to help retain it in place. Alternately, the tab 24 may be provided with an adhesive surface allowing the tab to be directly secured to the patient. In such an execution, the adhesive surface may be covered with a removable member such as those used on bandages to allow for convenient storage and handling. After insertion of one or two devices 3 into the oral cavity, the surgical procedure is performed once the patient is adequately anesthetized. After being anesthetized, an LMA or an endotracheal tube may be inserted into the oral cavity as is known in the art and preferably is inserted prior to insertion of the device 3. After the surgical procedure is completed, the patient is allowed to wake up while retaining the device(s) 3 in place between the gums. Two of the devices may be secured together with their respective tabs or with a common tab. After the patient has adequately awakened, the device may be removed from the oral cavity. In the event the tab is secured to the patient, it is separated from the patient prior to removal of the device. The device 3 may then be disposed of in an appropriate manner.

FIG. 5 shows an additional embodiment of the present invention. This embodiment may be utilized in any of the embodiments of the invention. One or more sensors 81 are carried by the pillow 71 and are operable to sense a condition or change in condition in the oral cavity such as the patient's temperature. Also, on occasion, a patient will expectorate bile or stomach contents which can eventually get into the lungs causing damage due to acidity thereof. The sensor 81 can be connected to an apparatus such as a monitor 83 which would sound an alarm or provide some other visual or audio signal indicative of the fluid coming into the mouth. The presence of such fluid can be indicated by a change in pH, a change in the moisture content of the pillow or by sensing for certain gases in the oral cavity. In a preferred embodiment, the sensor 81 would sense for a change in acidity and a signal from the monitor 83 would be provided to surgical personnel to indicate the presence of such fluid allowing the personnel to remove or otherwise handle the expectorated fluid. The sensor 81 may also be operable to sense for moisture, e.g., by a change in conductance. The sensor 81 may also be operable to sense a patient's temperature. Such a temperature sensor can be a thermocouple, which can be shielded for safety. The sensor 81 could also sense a plurality of such conditions. The shielding of the sensor 81 can be a resilient cover, such as a soft plastic, to protect the teeth and oral cavity tissue from damage and the shield can be positioned to contact tissue in the oral cavity. The sensor 81 can also be shielded by being imbedded inside the pillow. The sensor 81 can extend through the pillow 71 from end-to-end extending from the ends if desired. If shielding is not desired, the sensor 81 may be affixed to the exterior of the pillow as desired. Shielding may be partial or total.

The use of the described pillow permits easy temporary mounting of the sensor to the pillow as well as easy adjustment of the position of the sensor.

As is evident from the foregoing description, certain aspects of the present invention are not limited by the particular details of the examples illustrated herein and it is therefore contemplated that other modifications and applications, or equivalents thereof, will occur to those skilled in the art. It is accordingly intended that the claims shall cover all such modifications and applications that do not depart from the spirit and scope of the present invention.

Other aspects, objects and advantages of the present invention can be obtained from a study of the drawings, the disclosure and the appended claims.

The invention claimed is:

1. An intra-oral cavity device for preventing contact between upper and lower teeth and/or gums of an anesthetized patient, said device comprising:
    an elongate pillow sized and configured to fit inside the patient's mouth, said elongate pillow having at least an exterior portion of which is fibrous material and defining an interior and having material positioned in the interior that is at least one of porous and absorbent, said pillow having at least one transverse dimension in the range of between about ⅜ inch and about 1 inch and a length in the range of between about 1½ inches and about 3½ inches; and
    means cooperating with the fibrous material for preventing the fibrous material from separating from the pillow and thereby retaining the pillow as a monolithic structure.

2. An intra-oral cavity device as set forth in claim 1 wherein said fibrous material includes a sheet of fabric at least on an exterior of the pillow.

3. An intra-oral cavity device as set forth in claim 2 wherein the material in the interior of the pillow also includes at least one sheet of fabric.

4. An intra-oral cavity device as set forth in claim 2 wherein said means includes an adhesive backed retainer at least partially wrapped around an exterior surface of the pillow and being adhesively secured to an exterior layer of an exterior fibrous sheet.

5. An intra-oral cavity device as set forth in claim 4 wherein the retainer includes an adhesive backed polymeric sheet extending substantially the entire length of the pillow and wrapped substantially completely around an exterior surface of the pillow.

6. An intra-oral cavity device as set forth in claim 1 including a tab projecting from the pillow and adapted for engagement by surgical personnel for assisting in removal of the pillow from an oral cavity.

7. An intra-oral cavity device as set forth in claim 6 wherein said tab includes a fabric ribbon having an adhesive coated surface thereof secured to an interior portion of the pillow.

8. An intra-oral cavity device as set forth in claim 7 wherein said ribbon has a portion thereof adhesively secured to itself providing at least two exposed surfaces that are substantially adhesive free for engagement by surgical personnel.

9. An intra-oral cavity device as set forth in claim 1 wherein the fibrous material includes an outer sheet of fabric in the form of a tube and containing fibrous material in the interior.

10. An intra-oral cavity device as set forth in claim 9 wherein the fibrous material in the tube includes random oriented fibers.

11. An intra-oral cavity device as set forth in claim 9 wherein the fibrous material in the tube includes at least one sheet of fibrous material.

12. An intra-oral cavity device as set forth in claim 9 wherein said tube has a selectively closeable end portion closeable by a drawstring with said drawstring functioning as a gripping tab for gripping by surgical personnel.

13. An intra-oral cavity device as set forth in claim 1 wherein the fibrous material includes woven fabric.

14. An intra-oral cavity device as set forth in claim 1 wherein the fibrous material includes a knit sheet of material.

15. An intra-oral cavity device as set forth in claim 1 wherein the fibrous material includes a felt sheet of material.

16. An intra-oral cavity device as set forth in claim 1 wherein the device carries a sensor operable for detecting a change in the condition in the oral cavity and provide a signal indicative of said change.

17. A method of treating a surgical patient:
    preparing a patient for surgery, said patient having an oral cavity;
    placing at least one pillow in the oral cavity prior to at least a portion of surgery with at least a portion of the pillow being intra-oral, said pillow being elongate and comprising fibrous material, and means cooperating with the fibrous material for preventing the fibrous material in the pillow from separating from the pillow and thereby retaining the pillow as a monolithic structure while in the oral cavity, a portion of the intra-oral portion being positioned between a patient's gums to maintain teeth and/or gums in the oral cavity spaced apart during at least a portion of the surgery;
    performing surgery on the patient; and
    removing the pillow from the oral cavity.

18. A method as set forth in claim 17 including moistening the at least one pillow prior to placing it into the oral cavity.

* * * * *